(12) United States Patent
Fenn et al.

(10) Patent No.: US 9,247,944 B2
(45) Date of Patent: Feb. 2, 2016

(54) VERTEBRAL SCRAPER

(71) Applicant: Synthes USA, LLC, West Chester, PA (US)

(72) Inventors: Matthew Fenn, West Chester, PA (US); Stephen Heiman, Exton, PA (US); Sean Saidha, East Fallowfield, PA (US); Gregory Walters, Mount Royal, NJ (US); Michael White, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 299 days.

(21) Appl. No.: 13/707,954

(22) Filed: Dec. 7, 2012

(65) Prior Publication Data

US 2014/0163560 A1 Jun. 12, 2014

(51) Int. Cl.
*A61B 17/16* (2006.01)
*A61F 2/46* (2006.01)
*A61F 2/44* (2006.01)

(52) U.S. Cl.
CPC ......... *A61B 17/1659* (2013.01); *A61B 17/1671* (2013.01); *A61F 2/4684* (2013.01); *A61F 2/4455* (2013.01)

(58) Field of Classification Search
CPC ............ A61B 17/1659; A61B 17/1671; A61F 2/4455
USPC .............................. 606/79–85, 86 R
See application file for complete search history.

(56) References Cited

U.S. PATENT DOCUMENTS

| 6,517,544 B1 * | 2/2003 | Michelson ...................... 606/80 |
| 6,736,821 B2 * | 5/2004 | Squires et al. .................. 606/87 |
| 6,884,246 B1 * | 4/2005 | Sonnabend et al. ............ 606/80 |
| 2011/0071527 A1 * | 3/2011 | Nelson et al. ................... 606/85 |

* cited by examiner

*Primary Examiner* — Christopher Beccia
(74) *Attorney, Agent, or Firm* — Meunier Carlin & Curfman LLC

(57) ABSTRACT

A trialing and preparation system for preparing a disc space between two adjacent vertebrae is provided. The system includes a guide shaft, a trialing cage or spacer, a scraper and a driving shaft. The guide shaft supports the trialing spacer within the disc space and may include an angular adjustment for such access. The scraper sleeves over the guide shaft into an abutting relationship with the adjacent vertebrae. The driving shaft is coupled to the scraper by a pivoting and reciprocation mechanism that allows angular adjustment of the scraper. Also, reciprocation of the driving shaft reciprocates the scraper through a limited sweep of motion to remove osteophytes from the vertebrae.

39 Claims, 6 Drawing Sheets

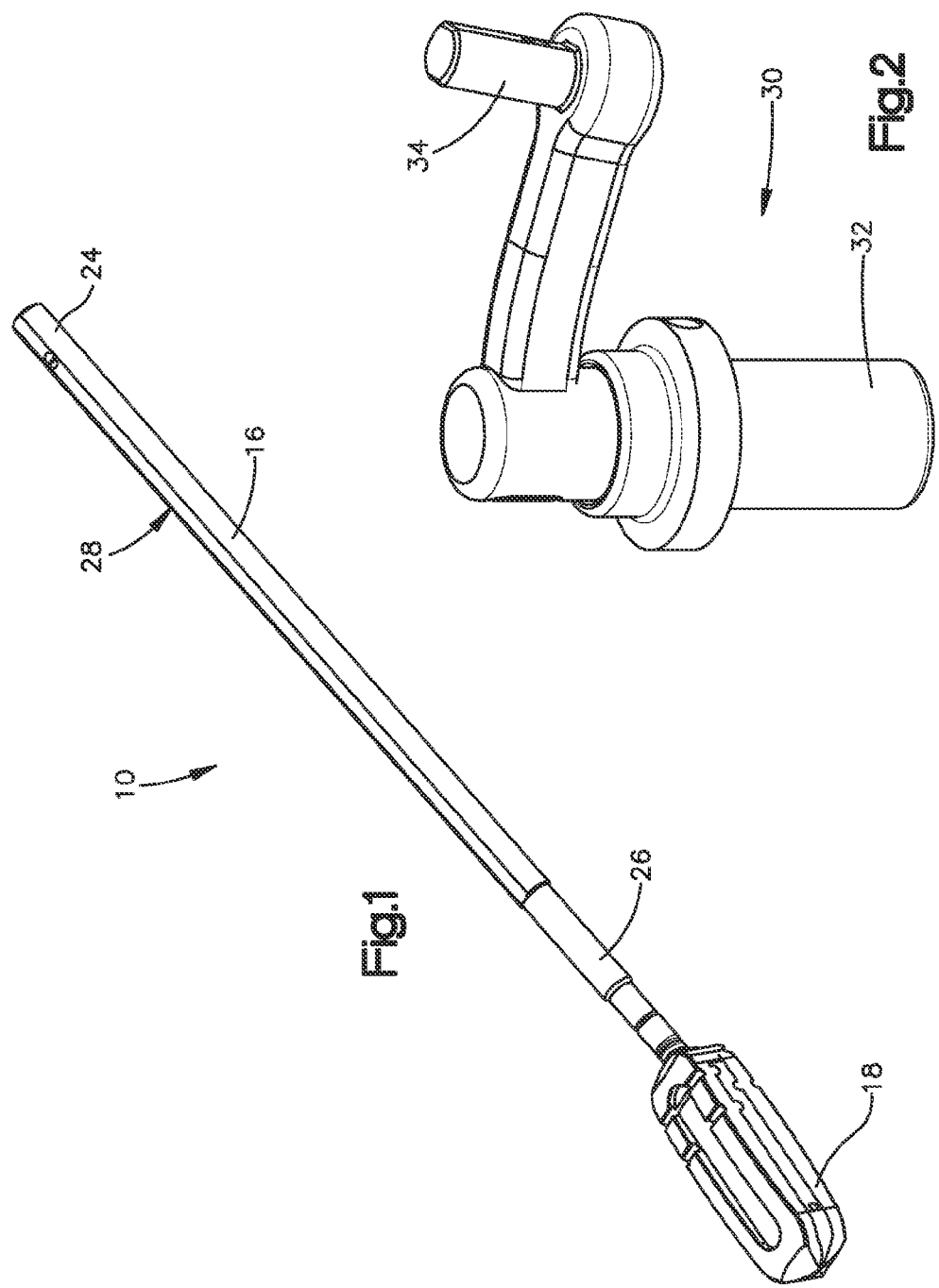

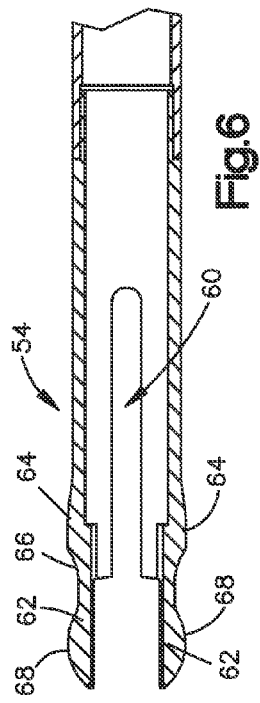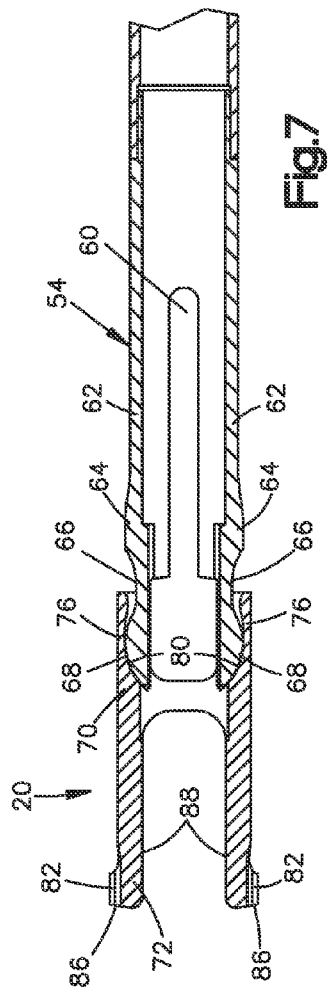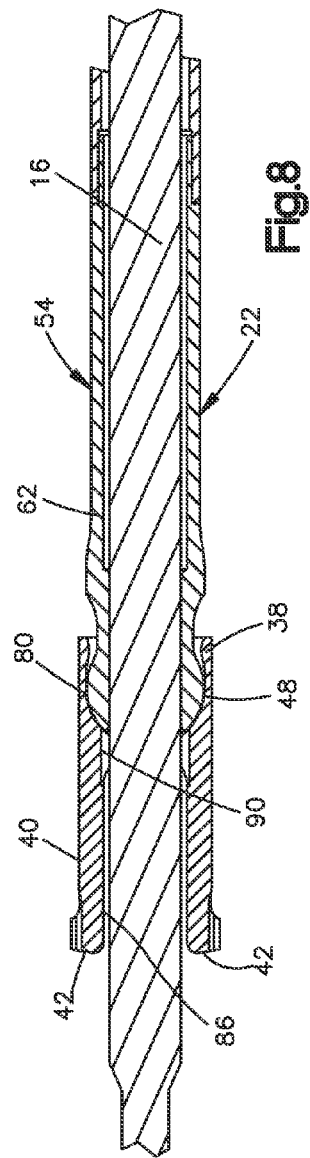

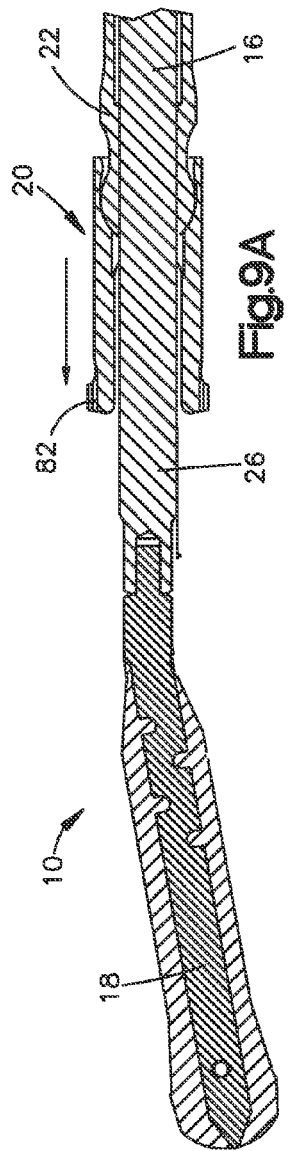
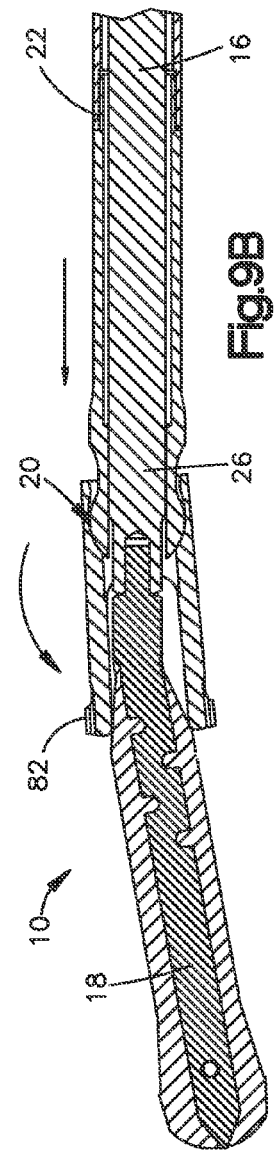
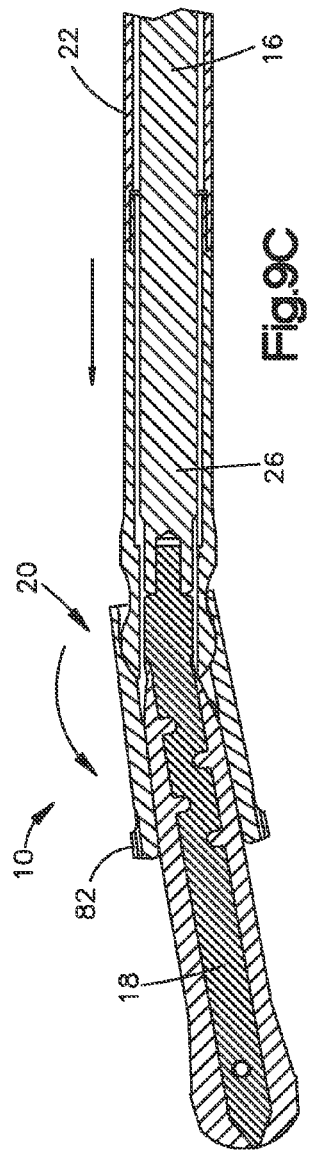

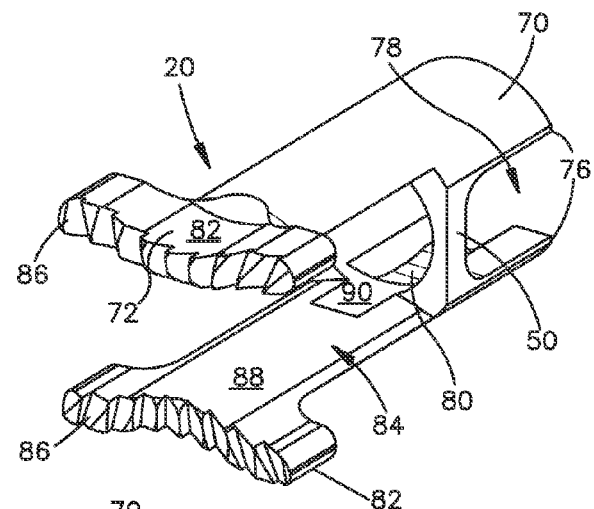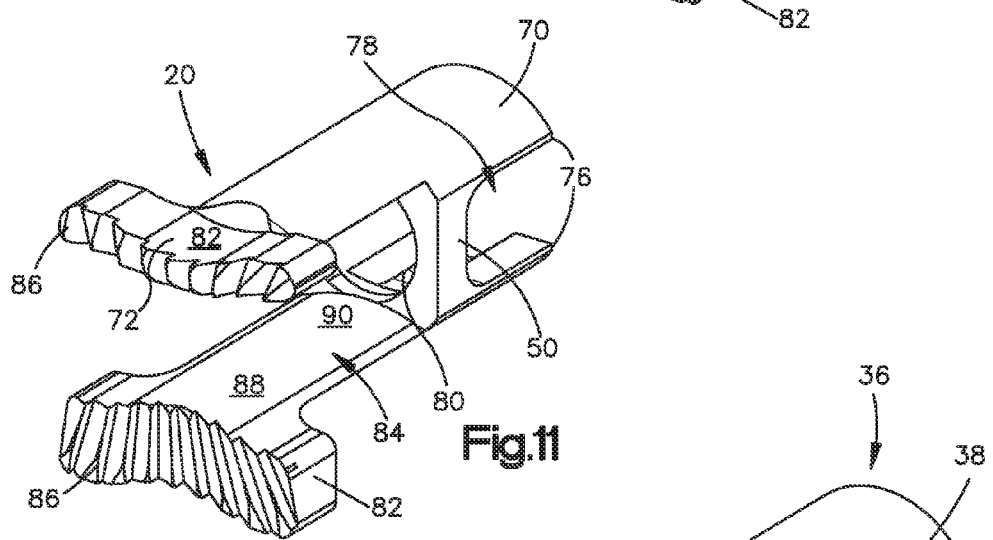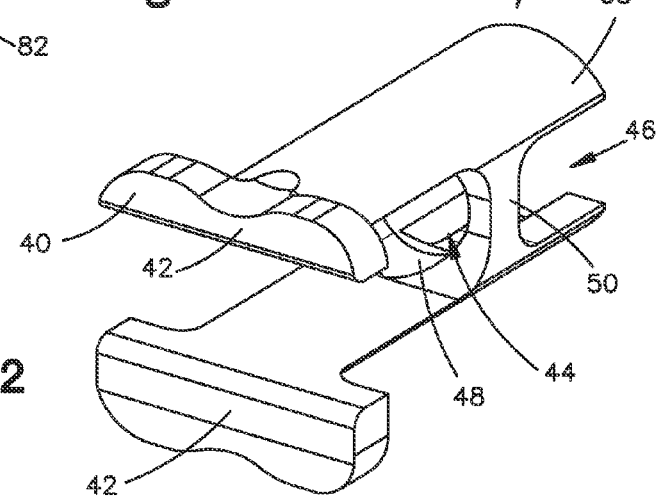

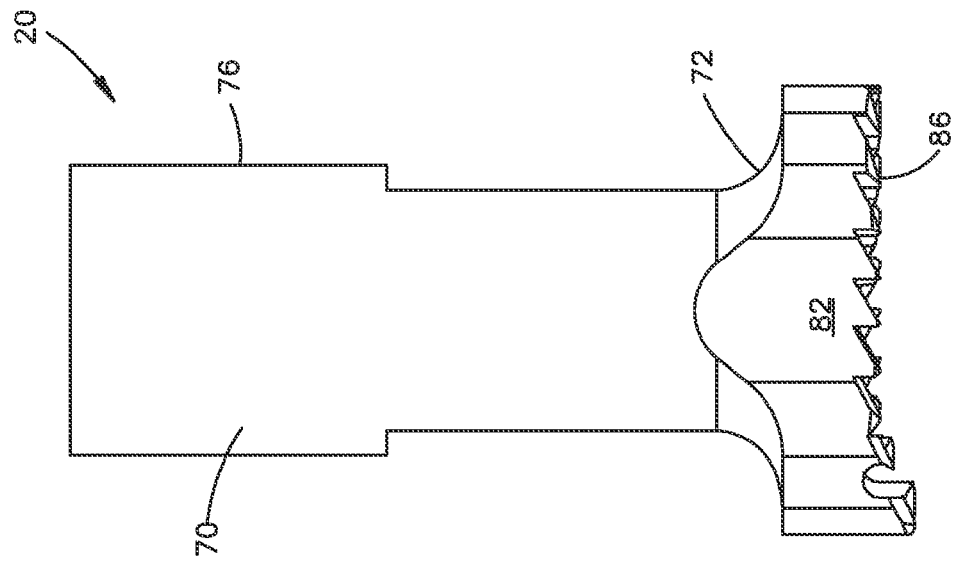
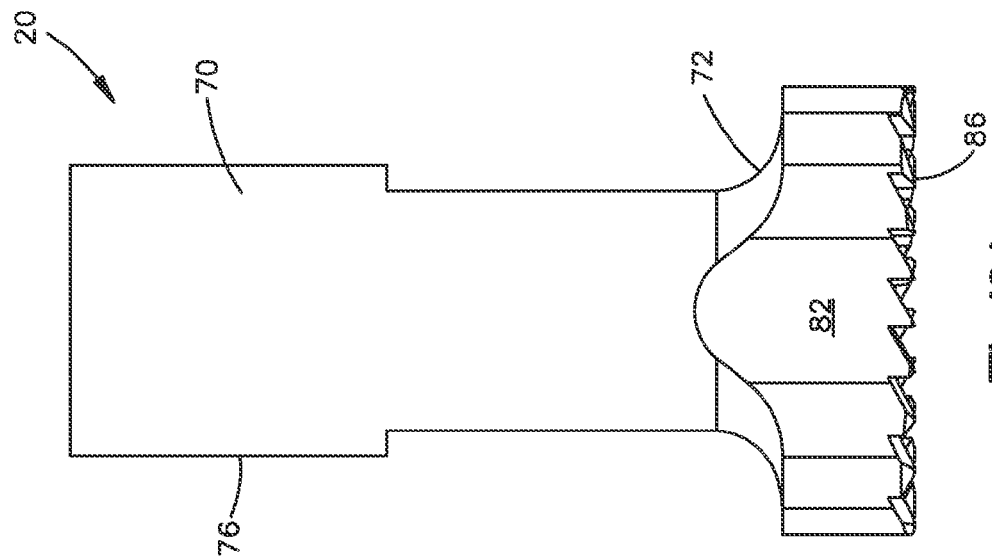

VERTEBRAL SCRAPER

BACKGROUND

Laterally inserted fixation assemblies for intervertebral discs typically use multiple screws to ensure fixation. Prior to implant insertion, the height of the implant is selected based on insertion of a range of trial implants. Accurate trialing can be inhibited by the presence of osteophytes that build up around the peripheral edges of the vertebral end plates. Osteophyte removal, for example, can be done with a chisel. But, this is a time consuming procedure and it is difficult to control the amount of bone removed.

A need exists, therefore, for improvements in preparation of the disc space for fixation and, in particular, removal of osteophytes.

SUMMARY

Implementations of the present disclosure overcome the problems of the prior art by providing a scraper for use on a pair of adjacent vertebral bodies. The vertebral bodies have an intervening disc space wherein a guide shaft is positioned in or adjacent to the disc space. The scraper includes a body, scraping surface and reciprocation mechanism.

The body defines an opening configured to fit over the guide shaft and advance toward the distal end of the guide shaft until adjacent the vertebral bodies. The scraping surface is supported by the body against the vertebral bodies. The reciprocation mechanism is configured to reciprocate the body and the scraping surface through a limited sweep range to remove material from the vertebral bodies.

The reciprocation mechanism may include one or more cam surfaces supported by the body. The cam surfaces may partially define the opening and be configured to cam against the guide shaft. The cam surfaces may be positioned on opposite sides of the opening. A portion of the opening may have a closed periphery defined by a proximal portion of the body and the distal portion of the body may support the scraping surface. The cam surfaces, for example, may be convexly arced toward an axis of the body.

The distal portion of the body may include a pair of flanges including the scraping surfaces. The scraping surfaces may include an abrasion pattern, such as teeth with varied heights. Each of the flanges may have a T-shape (or hammer head shape) extending from the proximal portion of the body.

The proximal portion of the body may include a partially cylindrical shape defining the opening. And, the T-shaped flanges may extend opposite each other across an axis of the cylindrical shape of the body.

The reciprocation mechanism may include a driving shaft configured to couple to the body and reciprocate the body on the first cam surface against the guide shaft. The driving shaft may include a handle and an axial opening configured to slide over the guide shaft.

The body opening may be configured to slide over the guide shaft. And, the body may include an anti-rotation feature configured to block rotation of the body when positioned over a proximal end of the guide shaft. The anti-rotation feature, for example, may be a flat surface at least partially defining the opening and configured to overlay a flat surface on the proximal end of the guide shaft. The guide shaft may have a distal end with a curved surface that allows rotation of the body and anti-rotation feature.

The body may include a proximal end defining a bearing surface configured to rotationally interact with a bearing surface on a distal end of a driving shaft. The driving shaft may include an axial opening configured to sleeve over the guide shaft. The bearing surfaces may allow a pitch of the body to change relative to the driving shaft.

The distal end of the guide shaft may include a trialing spacer configured for insertion into the disc space. The opening of the body may be configured to slide over the trialing spacer.

The distal end of the guide shaft may also be configured to mount to the trialing spacer so that an axis of the guide shaft is at an angle to an axis of the trialing spacer. For example, the pitch of the body relative to the driving shaft may adjust to approximate the angle of the guide shaft relative to the trialing spacer as the body is advanced off of the distal end of the guide shaft onto the trialing spacer.

The bearing surfaces of the body and the driving shaft may lock into each other when the body and the driving shaft are advanced over the guide shaft.

In another implementation, a trialing kit may include a guide shaft, a trialing spacer and a scraper. The trialing kit may also include a driving shaft or a trialing plate. These components may have the variations described above, for example, to facilitate trialing for implantation of a spacer block and plate.

A method of scraping a vertebral body may include positioning a guide shaft in or adjacent a disc space next to the vertebral body. The scraper body may be fitted over the guide shaft and advanced toward a distal end of the guide shaft until adjacent the vertebral body. A scraping surface of the scraper is reciprocated through a limited sweep range to remove material from the vertebral body.

The method may further include coupling a driving shaft to the scraper body and reciprocating the driving shaft to reciprocate the scraping surface.

The method may further include coupling a trialing spacer to a distal end of the guide shaft and inserting the trialing spacer into the disc space.

The method may also further include adjusting a pitch of the trialing spacer relative to the guide shaft to align the trialing spacer with the disc space.

And, the method may include adjusting a pitch of the scraper body to match the pitch of the guide shaft.

These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

FIG. 1 shows a perspective view of a system for preparing a disc space;

FIG. 2 shows a perspective view of an adaptor;

FIG. 6 shows an elevation view of a distal end of the driving shaft of FIG. 5;

FIG. 7 shows a cross-sectional view of the distal end of the driving shaft of FIG. 6 mated with a scraper;

FIG. 8 shows a cross-sectional view of the driving shaft and scraper of FIG. 7 sleeved over a guide shaft;

FIGS. 9A-9C show cross-sectional views of sleeving of a driving shaft and scraper in a distal direction over the guide shaft and a trial spacer;

FIG. 10 shows a perspective view of a scraper;

FIG. 11 shows a perspective view of another scraper;

FIG. 12 shows a perspective view of a trialing plate; and

FIGS. 13A and 13B show plan views of scrapers with varied tooth patterns.

DETAILED DESCRIPTION

Figure 3:
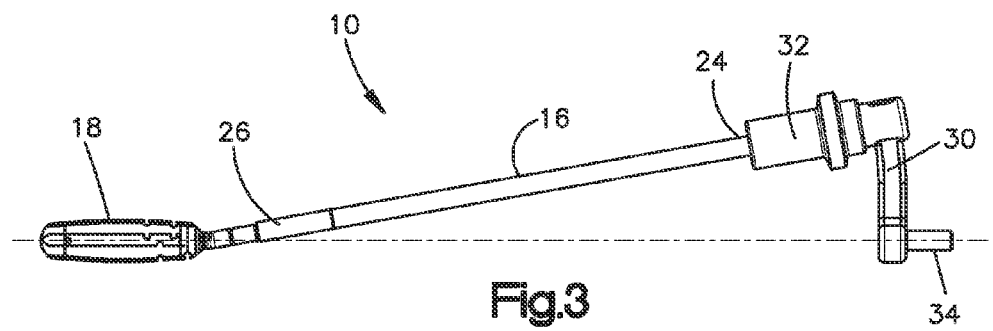
FIG. 3 shows a side elevation view of the system of FIG. 1 with the adaptor of FIG. 2.

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

A trialing and preparation system 10, for preparing a disc space between two adjacent vertebrae, is shown in FIG. 1. The system 10 includes a guide shaft 16, a trialing cage or spacer 18, a scraper 20 and a driving shaft 22, as shown in FIGS. 1 and 9. The guide shaft 16 supports the trialing spacer 18 within the disc space 12 and may include an angular adjustment for such access. The scraper 20 slides over the guide shaft 16 into an abutting relationship with the adjacent vertebrae 14. The driving shaft 22 is coupled to the scraper 20 by a pivoting and reciprocation mechanism that allows angular adjustment of the scraper 20. Also, reciprocation of the driving shaft 22 reciprocates the scraper 20 through a limited sweep of motion to remove osteophytes from the vertebrae 14.

Returning to FIG. 1, the guide shaft 16 has an elongate structure that includes a proximal portion 24 and a distal portion 26. The proximal portion has a non-round cross-section including elongate flat surfaces 28 that extend about 80% the length of the guide shaft 16 before transitioning to the distal portion 26. The flat surfaces 28 are on opposite sides of the proximal portion 24. A proximal-most end of the proximal portion 24 includes an additional pair of opposing flat surfaces 28. The proximal-most end is configured to mate with an adaptor 30, as shown in FIG. 3.

The distal portion 26 of the guide shaft 16 has a cylindrical cross-section at a first, larger diameter and then near the distal-most end tapers to a second smaller diameter. As shown in the cross-section of FIGS. 9A-9C, the distal portion 26 has a slight bend and necks down into a threaded distal-most end that is configured to mate with the trialing spacer 18. Alternatively, the distal portion 26 of the guide shaft 16 could be welded to the trialing spacer 18. This connection secures the trialing spacer 18 to the guide shaft 16 for insertion into the disc space 12 with the (optional) angled configuration shown in FIGS. 1 and 3, for example. The angled configuration allows avoidance of otherwise intervening anatomy, such as the iliac crest, when inserting the trialing spacer 18 into the disc space 12. Also, the guide shaft 16 may have a smooth outer surface with no asperities on its outer profile to facilitate guidance of the scraper 20 and other devices, such as a trialing plate.

The guide shaft 16 may be angled in different directions depending upon the desired anatomy, or may be straight with no angle, or may have multiple angles at different axial locations.

The adaptor 30 includes cylindrical body 32, and an impact peg 34, as shown in FIG. 2. The cylindrical body 32 defines a female-receptacle shaped to fit the non-circular cross-section of the proximal portion 24 of the guide shaft, as shown in FIG. 3. On an opposite flanged end of the cylindrical body 32, a bolt opening is configured to receive a fastener to secure one end of the impact peg 34.

The impact peg 34 extends at an angle to the orthogonal of the axis of the driving shaft 22. This geometry aligns the longitudinal axis of the trial spacer 18 with the axis of impaction on the handle 30, as shown in FIG. 3. In this manner, impaction of the impact peg 36 is in line with the disc space and normal (for one particular surgical approach) to the sagittal plane.

Figure 4:
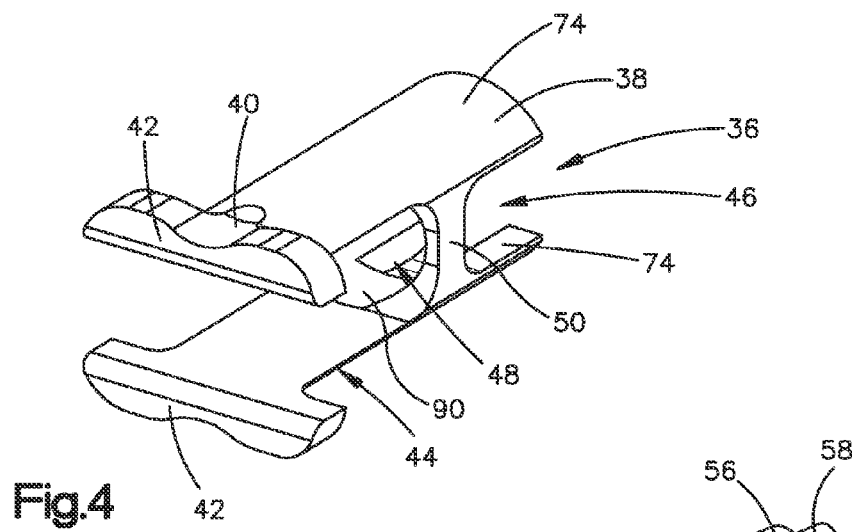
FIG. 4 shows a perspective view of a plate trial.

To determine the appropriate medial-lateral width of the eventual cage for implantation, a plate trial 36 can be used, such as the plate trial shown in FIG. 4. The plate trial 36 includes a proximal end 38 and a distal end 40. The proximal end 38 has a cylindrical shape defining an opening passing axially therethrough. The proximal end defines a lateral slot 46 and includes top and bottom, arc-shaped, convex bearing surfaces 48 partially defining the axial opening.

The lateral slot 46 extends through one or both sides of the wall structure of the proximal end 38 of the plate trial 36. When extending through both sides, the lateral slot 46 defines two legs 74. The two legs 74 have arc-shaped outer surfaces and include at least a portion of the convex bearing surfaces 48 at their inside diameters.

The distal end 40 of the plate trial 36 includes a pair of flanges 42 that extend from opposite sides of the axis of the plate trial. The flanges 42 have blunt, hammer-head shaped distal edges configured to abut the upper and lower vertebral bodies 14. Also, the distal end 40 of the plate trial defines a pair of lateral slots 44.

The plate trial 36 comes in different shapes and sizes to match the profile and height of the implant plate. The flanges 42 are contoured to the profile of the implant plate from the ventral and lateral perspective. Thus, when deployed, the plate trial 36 conveys some idea on fluoroscopic visualization (such as x-rays) or direct visualization of the likely size, positioning and configuration of the implantable plate and spacer combination.

Figure 5:
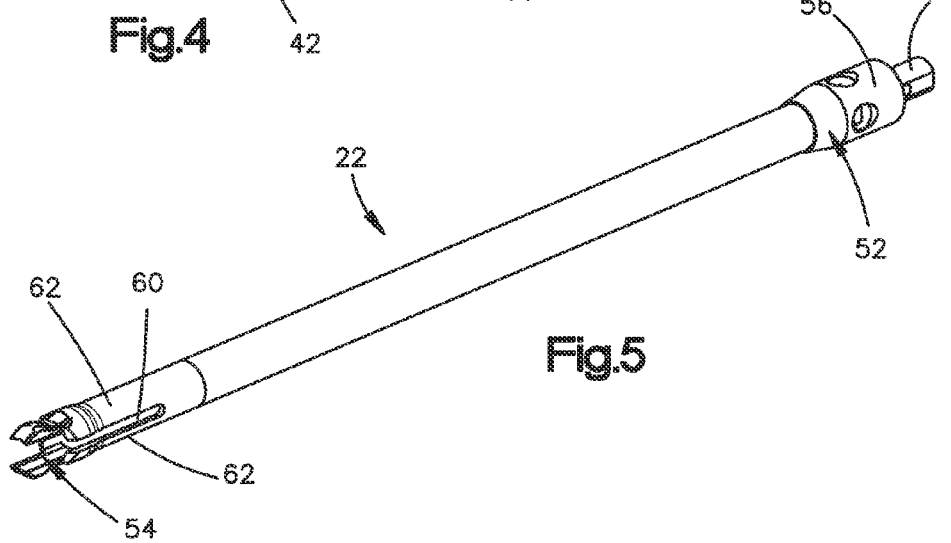
FIG. 5 shows a perspective view of a driving shaft.

As shown in FIGS. 5 and 6, the driving shaft 22 includes a proximal end 52 and a distal end 54. The proximal end 52 has an outer cylindrical flange 56 and a non-cylindrical mounting peg 58 extending proximally therefrom. Together, the flange 56 and mounting peg 58 are configured to cooperate with a palm grip push handle (not shown). The palm grip push handle provides for downward hand pressure on driving shaft 22 to aid in osteophyte removal.

The driving shaft 22 includes a central portion through which is defined a bore sized and shaped to allow passage over the guide shaft 16. The bore has a diameter that is wider than the widest diameter of the guide shaft 16 so that the driving shaft 22 may freely rotate around the driving shaft. Alternatively, some anti-rotation structure may be included to limit the rotation of the driving shaft relative to the guide shaft. In the illustrated implementation, an anti-rotation feature, however, is on the scraper 20, as will be described more hereinbelow. Or, there may be anti-rotation features on both the scraper 20 and shafts, or no anti-rotation feature at all.

The distal end 54 of the driving shaft 22, as shown in FIGS. 6 and 7, defines a longitudinal slot 60 that extends through both walls and axially out to the free end of the driving shaft. This longitudinal slot 60 bifurcates the distal end 54, which has a tubular shape, into two leg portions 62. The leg portions start at their proximal ends with a simple arc-shaped cross-section. But, moving distally, the leg portions 62 bulge outwards smoothly to a larger diameter 64 before transitioning into a concave taper 66. Moving further distally, the diameter of the leg portions 62 form convex, arc-shaped bearing surfaces 68.

The bearing surfaces 68 have positive shapes with a slightly smaller diameter of the similar negative shapes of the bearing surfaces 48 of the plate trial 36. This, along with the ability of the legs 62 to deflect, facilitates mounting the trial 36 on the distal end 54 of the driving shaft, as shown, for example, in FIG. 8. The legs 62 of the distal end 54 of the driving shaft 22 deflect somewhat for insertion into the proximal end 38 of the plate trial 36. Upon insertion, the relative shapes of the bearing surfaces 48, 68 nest with each other for a firm, but still separable, fit between the plate trial 36 and driving shaft 22.

It should be noted that the particular shapes, and positive-negative orientation of those shapes, could be changed or reversed as long as there is some type of relative movement of the plate trial 36 and driving shaft 22. This also applies to the bearing surfaces of the driving shaft and scraper, as described below.

Advantageously, as shown in FIG. 8, the longitudinal slot 60 allows the legs 62 to flex inwardly to attach the driving shaft 22 to the scraper. Conversely, the passage of the guide shaft 16 urges the legs 62 back to their normal position and pushes the positive, convex bearing surfaces 68 into the negative concave bearing surfaces 48. Stated differently, the guide shaft 16 inhibits collapse of the legs 62.

Because the proximal inside diameter of the trialing plate 36 is smaller than the largest outside diameter of the bearing surfaces 48, the bearing surfaces 48, 68 become fit into each other as they are slid over the guide shaft 16 because collapse of the legs 62 is inhibited. This locks together, but still allows relative pitch rotation (at least) of the trialing plate 36 as it is advanced over the guide shaft 16 and onto the angled trialing block or spacer 18, as shown in FIGS. 9A-9C. Optionally, the trialing plate 36 may also have some limited translations with respect to the driving shaft 22.

Advantageously, the trialing plate 36 helps the healthcare worker to size the implant by advancing it to a point where it is blocked by the adjacent vertebra 14. The length, then, of the trial spacer 18 extending past the distal end of the trial plate 35 approximates the length of the disc space. For example, once the plate trial 35 has been placed over the trial cage or spacer 18 and resides on the lateral portion of the vertebral body, the surgeon can measure the width of cage trial beyond the trial plate. The surgeon positions the distal portion of the cage trial 18 on the contralateral side of the vertebral body. The surgeon then uses fluoroscopy, and incremental notches located on the cage trial 18, to determine the known length from distal tip of trialing spacer 18.

As mentioned above, however, osteophytes may inhibit or affect the measurements. The osteophytes, for example, may extend laterally further than the original vertebral body. The surgeon may therefore opt to deploy the scraper 20 to remove the osteophytes. For example, should the surgeon encounter osteophyte on the ipsilateral portion of the vertebral body and they present a hindrance to appropriate trialing (and hence implant placement), the plate trial can be removed from the guide shaft. In place of the plate trial, a corresponding osteophyte removal tool (e.g., the scraper 20) can be added and retained in a similar manner to the plate trial.

The scraper 20 includes mostly similar geometry to the plate trial 36, e.g., the scraper includes a proximal end 70 and a distal end 72. The proximal end 70 may define a slot 78 which may extend through one or both walls so that the proximal end includes legs 76. The proximal end 70 and, if present, the legs 76, may also include the same cam or bearing surfaces 80 on their inside diameters. The distal end 72 includes the pair of hammer head shaped flanges 82 separated by lateral slots 84.

Exceptions to the similarities between the scraper 20 and the plate trial 36 include provision of scraping or abrasion surfaces 86 at the distal free edges of the flanges 82. For example, as shown in FIGS. 10, 11, 13A and 13B, the abrasion surfaces 86 include a plurality of teeth extending outward, some with varying heights. These teeth facilitate cutting and scraping away of the osteophytes at the end plate borders of the lateral edges of the vertebra using the pivoting motion described below. In one example, the teeth of the abrasion surfaces 86 may be 1 mm high and at an angle of 60 degrees to the longitudinal axis of the scraper.

It should be noted that the abrasion surfaces 86 could have a range of configurations depending upon such factors are the rate of bone removal, osteophyte geometry, desired final geometry, desired smoothness of the scraped surfaces, etc. Other abrasion surface geometries may include herringbone, knurled, grit, regular and irregular heights and patterns. Height variations are shown in FIG. 13B where the teeth are longer on one lateral edge than toward the middle and other lateral edge of the flanges 32. FIG. 13A, on the other hand, shows a relatively constant height.

Variation of the heights and cutting surfaces can create the depicted contoured lateral aspect of the abrasion surfaces 86. Advantageously, these contours facilitate reaming, at minimum, the lateral profile of the implant plate. Also, the asymmetric contours shown are configured to replicate the contour of asymmetric implant plates. Other cutting or abrasion surface shapes include planar surfaces or different curves to maximize or match the profile of the cutout to the profile of the implant plate.

The proximal end 70 of the scraper 20 also varies from the plate trial 36 by having bearing or cam surfaces 88 on the inside diameter of the distal end 72. For example, the cam surfaces 88 may be rounded or arc-shaped surfaces, shown in FIGS. 10 and 11. The cam surfaces 88 are rounded or curved in a different direction (transverse to the axis of the scraper 20) than the bearing surfaces 80 or 68 (which curve in the axial direction of the scraper or driver).

In contrast, the inside surfaces of the distal end 40 plate trial 36 are flat, as shown in FIG. 12. The flat surfaces of the distal end 40 are configured to abut the intervening trialing spacer 18 flat surfaces when the distal end 54 of the plate trial 36 is slipped over trialing spacer 18, as shown in FIGS. 9A-9C. These matching surfaces (which could also match with other non-flat shapes, such as positive and negative arc shapes) lock the plate trial 36 from rotating relative to the trialing spacer 18 during measurements.

The system 10 may also include anti-rotation features such as flats 28 on the outside of guide shaft 16 and flats on the inside surface of the distal end 54 of the driving shaft 22. While sliding axially along the guide shaft 16, the flats inside distal end 54 interact with the flat surfaces 28 on opposite sides of the proximal portion 24 of the guide shaft 16. These flats inhibit rotation of the plate trial 36 or scraper 20 mounted at the distal end 54 relative to the guide shaft 16 until reaching the distal end of the guide shaft. This facilitates orientation of the plate trial 36 or scraper 20 as it approaches the trialing spacer 18 so that the lateral slots are oriented with the lateral extension of the trialing spacer 18. Notably, the flats could be other non-circular surfaces and still inhibit rotation to some extent or entirely.

Other surfaces may include flats or other antirotation features (pegs for example) to mediate relative rotation of components of the system 10. For example, the scraper 20 may include internal flats 90 that interact with the external flats 28 of the guide shaft 16 to inhibit relative rotation.

The cam surfaces 88, on the other hand, allow the scraper 20 to be rotationally swept or reciprocated through a limited range of motion. Thus the healthcare worker may thus sweep the abrasion surfaces 86 against the osteophytes in a limited sweep, reciprocating motion to remove the osteophytes.

Also advantageously, unlike prior art scrapers which are configured to fully rotate about a cylindrical cannula, the system 10 provides for scraping motions about non-circular cross-sections, such as the trialing spacer 18. Restated, the scraping motion provides non-circular osteophyte removal in the shape of the plate or trialing spacer 18. The lateral slots 84 allow the scraper 20 to be slipped over the rectangular cross-section of the trialing spacer 18. Thus, the system 10 facilitates placement of the scraper 20 over angled support structures (e.g., the transition between the guide shaft 16 and the trialing spacer 18) and scraping of osteophytes with the trialing spacer 18 resident in the disc space 12.

A number of aspects of the systems, devices and methods have been described. Nevertheless, it will be understood that various modifications may be made without departing from the spirit and scope of the disclosure. Accordingly, other aspects are within the scope of the following claims.

REFERENCE NUMBERS

10 system
12 disc space
14 vertebra
16 guide shaft
18 trialing spacer
20 scraper
22 driving shaft
24 proximal portion of guide shaft
26 distal portion of guide shaft
28 flat surfaces
30 adaptor
32 cylindrical body
34 impact peg
36 plate trial
38 proximal end of plate trial
40 distal end of plate trial
42 flanges of plate trial
44 lateral slots of distal end
46 lateral slot of proximal end
48 bearing surfaces of plate trial
50 web structure of plate trial
52 proximal end of driving shaft
54 distal end of driving shaft
56 cylindrical flange of driving shaft
58 mounting peg of driving shaft
60 longitudinal slot of driving shaft
62 leg portions of distal end of driving shaft
64 larger diameter of leg portions
66 concave taper of leg portions
68 bearing surfaces of driving shaft
70 proximal end of scraper
72 distal end of scraper
74 legs of plate trial
76 legs of scraper
78 lateral slot
80 bearing surfaces of scraper
82 flanges of scraper
84 lateral slots of scraper
86 abrasion surfaces
88 cam surfaces
90 anti-rotation feature That which is claimed:

1. A scraper for use on a pair of adjacent vertebral bodies having an intervening disc space wherein a guide shaft is positioned in or adjacent the disc space, the scraper comprising:
    a body defining an opening configured to fit over the guide shaft and advance toward the distal end of the guide shaft until adjacent the vertebral bodies;
    a scraping surface, the body configured to support the scraping surface against the vertebral bodies; and
    a reciprocation mechanism configured to reciprocate the body and the scraping surface through a limited sweep range to remove material from the vertebral bodies, the reciprocating mechanism configured to slide over the guide shaft and including:
        a driving shaft, a distal end of the driving shaft defining a bearing surface configured to rotationally interact with a corresponding bearing surface on a proximal end of the body; and
        an anti-rotation feature configured to block rotation of the reciprocating mechanism relative to the guide shaft, the anti-rotation feature including a flat surface at least partially defining an opening of the reciprocating mechanism and configured to overlay a flat surface on the guide shaft,
    wherein the guide shaft has a distal end with a curved surface that allows rotation of the body and anti-rotation feature.

2. A scraper of claim 1, wherein the reciprocation mechanism includes at least one cam surface supported by the body.

3. A scraper of claim 2, wherein the at least one cam surface includes a first cam surface at least partially defining the opening and configured to cam against the guide shaft.

4. A scraper of claim 3, wherein the at least one cam surface includes a second cam surface at least partially defining the opening and configured to cam against the guide shaft.

5. A scraper of claim 4, wherein the first and second cam surfaces are positioned on opposite sides of the opening.

6. A scraper of claim 5, wherein a portion of the opening has a closed periphery defined by a proximal portion of the body and a distal portion of the body supports the scraping surface.

7. A scraper of claim 6, wherein the cam surfaces are convexly arced toward an axis of the body.

8. A scraper of claim 7, wherein the distal portion of the body includes a pair of flanges.

9. A scraper of claim 8, wherein the scraping surface includes an abrasion pattern.

10. A scraper of claim 9, wherein the abrasion pattern includes teeth.

11. A scraper of claim 10, wherein the teeth have varied heights.

12. A scraper of claim 8, wherein each of the flanges has a T-shape extending from the proximal portion of the body.

13. A scraper of claim 12, wherein the proximal portion of the body includes at least a partially cylindrical shape defining the opening.

14. A scraper of claim 13, wherein the T-shape flanges extend opposite each other across the axis of the body.

15. A scraper of claim 3, wherein the reciprocation mechanism includes a driving shaft configured to couple to the body and reciprocate the body on the first cam surface against the guide shaft.

16. A scraper of claim 15, wherein the driving shaft includes a handle.

17. A scraper of claim 15, wherein the driving shaft includes an axial opening configured to sleeve over the guide shaft.

18. A scraper of claim 1, wherein the driving shaft includes an axial opening configured to sleeve over the guide shaft.

19. A scraper of claim 18, wherein the bearing surfaces allow a pitch of the body to change relative to the driving shaft.

20. A scraper of claim 19, wherein the distal end of the guide shaft includes a trialing spacer configured for insertion into the disc space and the opening of the body is configured to sleeve over the trialing spacer.

21. A scraper of claim 20, wherein the distal end of the guide shaft is configured to mount to the trialing spacer so that an axis of the guide shaft is at an angle to an axis of the trialing spacer.

22. A scraper of claim 21, wherein the pitch of the body relative to the driving shaft adjusts to approximate the angle of the guide shaft relative to the trialing spacer as the body is advanced off of the distal end of the guide shaft onto the trialing spacer.

23. A scraper of claim 22, wherein the bearing surfaces of the body and the driving shaft lock into each other when the body and driving shaft are advanced over the guide shaft.

24. A trialing kit for preparing an intervening disc space between a pair of adjacent vertebral bodies, the trialing kit comprising:
a guide shaft configured for positioning in or adjacent the disc space, the guide shaft including a distal end;
a trialing spacer configured for association with the distal end of the guide shaft and insertion into the disc space; and
a scraper having:
a body defining an opening configured to fit over the guide shaft and the trialing spacer and advance toward the distal end of the guide shaft until adjacent the vertebral bodies, the body including a proximal end defining a bearing surface configured to rotationally interact with a corresponding bearing surface on a distal end of the driving shaft;
a scraping surface, the body configured to support the scraping surface against the vertebral bodies; and
a reciprocation mechanism configured to reciprocate the body and the scraping surface through a limited sweep range to remove material from the vertebral bodies, the reciprocation mechanism configured to slide over the guide shaft and including an anti-rotation feature configured to block rotation of the reciprocation mechanism relative to the guide shaft, the anti-rotation feature including a flat surface at least partially defining an opening of the reciprocation mechanism and configured to overlay a flat surface of the guide shaft;
wherein the distal end of the guide shaft has a curved surface that allows rotation of the body of the scrapper and the anti-rotation feature.

25. A trialing kit of claim 24, wherein the reciprocation mechanism includes at least one cam surface supported by the body.

26. A trialing kit of claim 25, wherein the at least one cam surface includes a first cam surface at least partially defining the opening and configured to cam against the guide shaft.

27. A trialing kit of claim 26, wherein the at least one cam surface includes a second cam surface at least partially defining the opening and configured to cam against the guide shaft.

28. A trialing kit of claim 27, wherein the first and second cam surfaces are positioned on opposite sides of the opening.

29. A trialing kit of claim 28, wherein a portion of the opening has a closed periphery defined by a proximal portion of the body and a distal portion of the body supports the scraping surface.

30. A trialing kit of claim 29, wherein the cam surfaces are convexly arced toward an axis of the body.

31. A trialing kit of claim 30, wherein the distal portion of the body includes an abrasion pattern with varied heights.

32. A trialing kit of claim 28, further comprising a driving shaft configured to couple to the body and reciprocate the body on the cam surfaces against the guide shaft.

33. A trialing kit of claim 32, wherein the driving shaft includes an axial opening configured to sleeve over the guide shaft.

34. A trialing kit of claim 33, wherein the guide shaft has a distal end with a curved surface that allows rotation of the body.

35. A method of scraping a vertebral body, the method including:
positioning a guide shaft in or adjacent a disc space next to the vertebral body;
fitting a scraper body over the guide shaft;
advancing the scraper body toward a distal end of the guide shaft until adjacent the vertebral body;
coupling a driving shaft to the scraper body by sliding the driving shaft over the guide shaft and positioning a bearing surface included at a proximal end of the body adjacent to a corresponding bearing surface on a distal end of the driving shaft such that the body bearing surface and the driving shaft bearing surface are configured to rotationally interact, the driving shaft including an anti-rotation feature configured to block rotation of the driving shaft relative to the guide shaft, the anti-rotation feature including a flat surface at least partially defining an opening of the driving shaft and configured to overlay a flat surface on the guide shaft;
reciprocating a scraping surface of the scraper body through a limited sweep range to remove material from the vertebral body, where the guide shaft has a distal end with a curved surface that allows rotation of the scraper body and the anti-rotation feature of the driving shaft.

36. A method of claim 35, further comprising reciprocating the driving shaft to reciprocate the scraping surface.

37. A method of claim 36, further comprising adjusting a pitch of the trialing spacer relative to the guide shaft to align the trialing spacer with the disc space.

38. A method of claim 37, further comprising coupling a trialing spacer to a distal end of the guide shaft and inserting the trialing spacer into the disc space.

39. A method of claim 38, further comprising adjusting a pitch of the scraper body to match the pitch of the guide shaft.

* * * * *